United States Patent [19]

Yamane

[11] Patent Number: 5,741,638

[45] Date of Patent: Apr. 21, 1998

[54] MICROTITER WELL FOR DETECTING NUCLEIC ACID

[75] Inventor: Akio Yamane, Kouda-Cho, Japan

[73] Assignee: Wakunaga Seiyaku Kabushiki Kaisha, Osaka-Fu, Japan

[21] Appl. No.: 358,995

[22] Filed: Dec. 19, 1994

Related U.S. Application Data

[63] Continuation of Ser. No. 4,572, Jan. 14, 1993, abandoned, which is a continuation-in-part of Ser. No. 722,673, Jun. 28, 1991, abandoned.

[30] Foreign Application Priority Data

Jun. 28, 1990 [JP] Japan ..................................... 2-170684

[51] Int. Cl.$^6$ ................................ C12Q 1/68; A61L 3/00
[52] U.S. Cl. ................................................................ 435/6
[58] Field of Search .................................. 435/6; 935/77, 935/78; 427/2, 58; 422/102; 436/809

[56] References Cited

PUBLICATIONS

Cook et al., Nucl. Acid. Res. 16:4077–4095 (1988) "Synthesis and Hybridization of a Series ...".
Nagata et al., FEBS 183: 379–382 (1985) "Quantification of Picogram Levels of Specific DNA ...".
Rosmvssen et al., Analytical Biochem 198:138–142 (1991) "Covalent Immobilization of DNA ...".
Murray et al., Mol. Biochem. Parasitol 30:209–216 (1988) "Cloning and Characterization of a Species–spefic ...".
Urdea et al, Nucleic Acid Res 16: 4937–4956 (1988).

*Primary Examiner*—Eggerton A. Campbell
*Attorney, Agent, or Firm*—Wenderoth, Lind & Ponack

[57] ABSTRACT

A microtiter well in which a single stranded nucleic acid including a plurality of sequences specifically hybridizalbe with a target nucleic acid is immobilized is disclosed. The single stranded nucleic acid is derived from a phage or a phage-plasmid. The microtiter well enables a target nucleic acid to be specifically detected with a high sensitivity and high efficiency and further enables the detection procedure to be automated.

4 Claims, 6 Drawing Sheets

5'
CACCTGACTCCTG[A]GGAGAAGTCTGCCGTT
GTGGACTGAGGAC[T]CCTCTTCAGACGGCAA
3'

βA

5'
CACCTGACTCCTG[T]GGAGAAGTCTGCCGTT
GTGGACTGAGGAC[A]CCTCTTCAGACGGCAA
3'

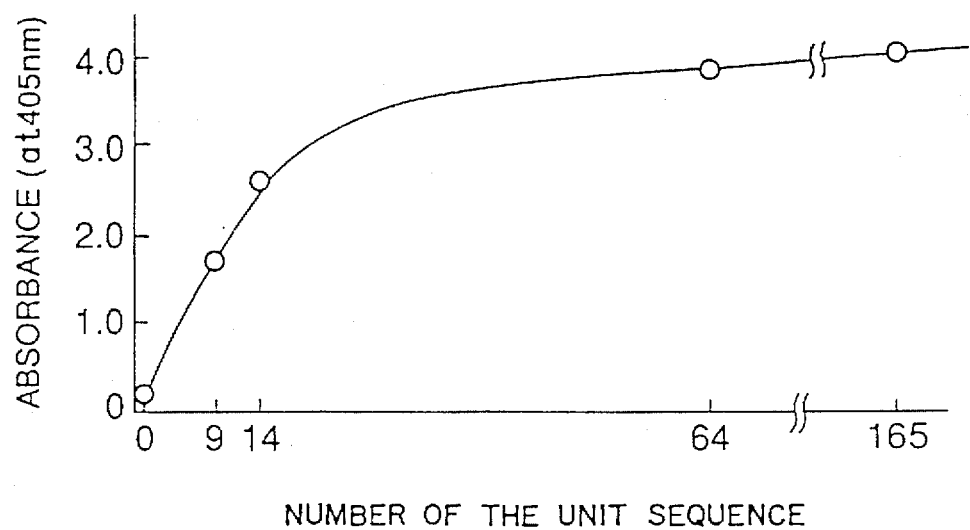
F I G . 5

```
              1          10          20          30
DRB1*0101   GGGGACACCCGACCACGTTTCTTGTGGCAG
DRB1*1201   ---------A--------------GA-T-C
DRB1*0901   ******************************
DRB5*0101   ----------------------CA-----
                                    CAGCAG 40          50          60
DRB1*0101   CTTAAGTTTGAATGTCATTTCTTCAATGGG
DRB1*1201   TC--C-GG---G---T--------------
DRB1*0901   *******************-----C---
DRB5*0101   GA-----A---G--------------C---
            GATAAGTA
              Probe A 70          80          90
DRB1*0101   ACGGAGCGGGTGCGGTTGCTGGAAAGATGC
DRB1*1201   ------------------A------G---CA-
DRB1*0901   -----------------AT---C-C---G--
DRB5*0101   ----------------C---C-C---GA-
                              GGTTACTGGAGAG
                                 Probe B
                              GTATCTGCACAGAGG
                                 Probe C
```

-: same as that of the uppermost sequence
*: unknown

FIG. 6

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION: /note= "sequence shown in Fig. 1 in 5'-3' direction"

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:1:

CAGCTGAATT CGGATCCGTC GACGGATCCG AATTCAGCTG    40

( 2 ) INFORMATION FOR SEQ ID NO:2:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION: /note= "having biotin at
            5' end with a spacer"

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:2:

ATTGTAATGG GCTCTGTCCG    20

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION: /note= "sequence shown in
            Fig. 3 in 5'-3' direction"

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:3:

```
CACCTGACTC CTGAGGAGAA GTCTGCCGTT          30
```

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:

(C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION: /note= "sequence shown in
                        Fig. 3 from 5'-3' direction"

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:4:

CACCTGACTC CTGTGGAGAA GTCTGCCGTT          30

(2) INFORMATION FOR SEQ ID NO:5:

(i) SEQUENCE CHARACTERISTICS:
                (A) LENGTH: 22 bases
                (B) TYPE: nucleic acid
                (C) STRANDEDNESS: single
                (D) TOPOLOGY: linear (ii) MOLECULE TYPE: other nucleic acid (iii) HYPOTHETICAL:

(iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:

-continued ( B ) LOCATION:
                ( C ) IDENTIFICATION METHOD:
                ( D ) OTHER INFORMATION:

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO:

( x i ) SEQUENCE DESCRIPTION: SEQ ID NO:5:

ACACAACTGT GTGTTCACTA GC                    2 2

( 2 ) INFORMATION FOR SEQ ID NO:6:

( i ) SEQUENCE CHARACTERISTICS:
                ( A ) LENGTH: 20 bases
                ( B ) TYPE: nucleic acid
                ( C ) STRANDEDNESS: single
                ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
                ( A ) ORGANISM:
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:
                ( A ) LIBRARY:
                ( B ) CLONE:

( v i i i ) POSITION IN GENOME:
                ( A ) CHROMOSOME/SEGMENT:
                ( B ) MAP POSITION:
                ( C ) UNITS:

( i x ) FEATURE:
                ( A ) NAME/KEY:
                ( B ) LOCATION:
                ( C ) IDENTIFICATION METHOD:
                ( D ) OTHER INFORMATION: /note="having biotin at
                        the 5'end with a spacer"

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO:

( x i ) SEQUENCE DESCRIPTION: SEQ ID NO:6:

CAACTTCATC CACGTTCACC    20

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION: /note= "sequence shown in
            Fig. 4 in 5'-3' direction"

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:7:

AGGTATGAGC AATTAAATGA CAGCTCA    27

( 2 ) INFORMATION FOR SEQ ID NO:8:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION: /note="having biotin at
                        the 5'end with a spacer"

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:8:

GCAACCAGAG ACAACTGATC                    20

(2) INFORMATION FOR SEQ ID NO:9:

(i) SEQUENCE CHARACTERISTICS:
                (A) LENGTH: 18 bases
                (B) TYPE: nucleic acid
                (C) STRANDEDNESS: single
                (D) TOPOLOGY: linear (ii) MOLECULE TYPE: other nucleic acid (iii) HYPOTHETICAL:

(iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:9:

CGG TTG CTG GAA AGA TGC    18

( 2 ) INFORMATION FOR SEQ ID NO:10:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:10:

CAG CAG GAT AAG TAT GAG        18

( 2 ) INFORMATION FOR SEQ ID NO:11:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:11:

GGC CGG GTG GAC AAC TAC        18

( 2 ) INFORMATION FOR SEQ ID NO:12:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:12:

TTG GAG CAG GTT AAA CAT                18

(2) INFORMATION FOR SEQ ID NO:13:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

```
        ( i x ) FEATURE:
                  ( A ) NAME/KEY:
                  ( B ) LOCATION:
                  ( C ) IDENTIFICATION METHOD:
                  ( D ) OTHER INFORMATION:

( x ) PUBLICATION INFORMATION:
                  ( A ) AUTHORS:
                  ( B ) TITLE:
                  ( C ) JOURNAL:
                  ( D ) VOLUME:
                  ( E ) ISSUE:
                  ( F ) PAGES:
                  ( G ) DATE:
                  ( H ) DOCUMENT NUMBER:
                  ( I ) FILING DATE:
                  ( J ) PUBLICATION DATE:
                  ( K ) RELEVANT RESIDUES IN SEQ ID NO:

( x i ) SEQUENCE DESCRIPTION: SEQ ID NO:13:

T   GAT   GAG   GAG   TAC   TGG   AA         1 8

( 2 ) INFORMATION FOR SEQ ID NO:14:

( i ) SEQUENCE CHARACTERISTICS:
                  ( A ) LENGTH: 18 bases
                  ( B ) TYPE: nucleic acid
                  ( C ) STRANDEDNESS: single
                  ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
                  ( A ) ORGANISM:
                  ( B ) STRAIN:
                  ( C ) INDIVIDUAL ISOLATE:
                  ( D ) DEVELOPMENTAL STAGE:
                  ( E ) HAPLOTYPE:
                  ( F ) TISSUE TYPE:
                  ( G ) CELL TYPE:
                  ( H ) CELL LINE:
                  ( I ) ORGANELLE:

( v i i ) IMMEDIATE SOURCE:
                  ( A ) LIBRARY:
                  ( B ) CLONE:

( v i i i ) POSITION IN GENOME:
                  ( A ) CHROMOSOME/SEGMENT:
                  ( B ) MAP POSITION:
                  ( C ) UNITS:

( i x ) FEATURE:
                  ( A ) NAME/KEY:
                  ( B ) LOCATION:
                  ( C ) IDENTIFICATION METHOD:
                  ( D ) OTHER INFORMATION:

( x ) PUBLICATION INFORMATION:
                  ( A ) AUTHORS:
                  ( B ) TITLE:
                  ( C ) JOURNAL:
                  ( D ) VOLUME:
                  ( E ) ISSUE:
                  ( F ) PAGES:
                  ( G ) DATE:
                  ( H ) DOCUMENT NUMBER:
                  ( I ) FILING DATE:
                  ( J ) PUBLICATION DATE:
                  ( K ) RELEVANT RESIDUES IN SEQ ID NO:
```

( x i ) SEQUENCE DESCRIPTION: SEQ ID NO:14:

GG TTA CTG GAG AGA CAC T        18

( 2 ) INFORMATION FOR SEQ ID NO:15:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:15:

TTC TTG GAG TAC TCT ACG         18

( 2 ) INFORMATION FOR SEQ ID NO:16:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:16:

TGG CAG GGT AAG TAT AAG    18

(2) INFORMATION FOR SEQ ID NO:17:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: other nucleic acid (iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
  (A) NAME/KEY:
  (B) LOCATION:
  (C) IDENTIFICATION METHOD:
  (D) OTHER INFORMATION:

(x) PUBLICATION INFORMATION:
  (A) AUTHORS:
  (B) TITLE:
  (C) JOURNAL:
  (D) VOLUME:
  (E) ISSUE:
  (F) PAGES:
  (G) DATE:
  (H) DOCUMENT NUMBER:
  (I) FILING DATE:
  (J) PUBLICATION DATE:
  (K) RELEVANT RESIDUES IN SEQ ID NO:

(xi) SEQUENCE DESCRIPTION: SEQ ID NO:17:

A GAC AGG CGG GCC CTG GT    18

(2) INFORMATION FOR SEQ ID NO:18:

(i) SEQUENCE CHARACTERISTICS:
    (A) LENGTH: 18 bases
    (B) TYPE: nucleic acid
    (C) STRANDEDNESS: single
    (D) TOPOLOGY: linear (ii) MOLECULE TYPE: other nucleic acid (iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

( x i ) SEQUENCE DESCRIPTION: SEQ ID NO:18:

G TAT CTG CAC AGA GGC AT    18

( 2 ) INFORMATION FOR SEQ ID NO:19:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:19:

TTG AAG CAG GAT AAG TTT    18

( 2 ) INFORMATION FOR SEQ ID NO:20:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

```
        ( v i ) ORIGINAL SOURCE:
                ( A ) ORGANISM:
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:
                ( A ) LIBRARY:
                ( B ) CLONE:

( v i i i ) POSITION IN GENOME:
                ( A ) CHROMOSOME/SEGMENT:
                ( B ) MAP POSITION:
                ( C ) UNITS:

( i x ) FEATURE:
                ( A ) NAME/KEY:
                ( B ) LOCATION:
                ( C ) IDENTIFICATION METHOD:
                ( D ) OTHER INFORMATION:

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO:

( x i ) SEQUENCE DESCRIPTION: SEQ ID NO:20:

TGC AGA CAC AAC TAC GGG        1 8

( 2 ) INFORMATION FOR SEQ ID NO:21:

( i ) SEQUENCE CHARACTERISTICS:
                ( A ) LENGTH: 20 bases
                ( B ) TYPE: nucleic acid
                ( C ) STRANDEDNESS: single
                ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
                ( A ) ORGANISM:
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:
                ( A ) LIBRARY:
                ( B ) CLONE:

( v i i i ) POSITION IN GENOME:
                ( A ) CHROMOSOME/SEGMENT:
                ( B ) MAP POSITION:
                ( C ) UNITS:
```

( i x ) FEATURE:
  ( A ) NAME/KEY:
  ( B ) LOCATION:
  ( C ) IDENTIFICATION METHOD:
  ( D ) OTHER INFORMATION: /note="having biotin at
    the 5'end with a spacer"

( x ) PUBLICATION INFORMATION:
  ( A ) AUTHORS:
  ( B ) TITLE:
  ( C ) JOURNAL:
  ( D ) VOLUME:
  ( E ) ISSUE:
  ( F ) PAGES:
  ( G ) DATE:
  ( H ) DOCUMENT NUMBER:
  ( I ) FILING DATE:
  ( J ) PUBLICATION DATE:
  ( K ) RELEVANT RESIDUES IN SEQ ID NO:

( x i ) SEQUENCE DESCRIPTION: SEQ ID NO:21:

TTCTTCAATG GGACGGAGCG   20

( 2 ) INFORMATION FOR SEQ ID NO:22:

( i ) SEQUENCE CHARACTERISTICS:
  ( A ) LENGTH: 22 bases
  ( B ) TYPE: nucleic acid
  ( C ) STRANDEDNESS: single
  ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
  ( A ) ORGANISM:
  ( B ) STRAIN:
  ( C ) INDIVIDUAL ISOLATE:
  ( D ) DEVELOPMENTAL STAGE:
  ( E ) HAPLOTYPE:
  ( F ) TISSUE TYPE:
  ( G ) CELL TYPE:
  ( H ) CELL LINE:
  ( I ) ORGANELLE:

( v i i ) IMMEDIATE SOURCE:
  ( A ) LIBRARY:
  ( B ) CLONE:

( v i i i ) POSITION IN GENOME:
  ( A ) CHROMOSOME/SEGMENT:
  ( B ) MAP POSITION:
  ( C ) UNITS:

( i x ) FEATURE:
  ( A ) NAME/KEY:
  ( B ) LOCATION:
  ( C ) IDENTIFICATION METHOD:
  ( D ) OTHER INFORMATION: /note="having biotin at
    the 5'end with a spacer"

( x ) PUBLICATION INFORMATION:
  ( A ) AUTHORS:
  ( B ) TITLE:
  ( C ) JOURNAL:
  ( D ) VOLUME:
  ( E ) ISSUE:
  ( F ) PAGES:
  ( G ) DATE:
  ( H ) DOCUMENT NUMBER:
  ( I ) FILING DATE:
  ( J ) PUBLICATION DATE:

( K ) RELEVANT RESIDUES IN SEQ ID NO:

( x i ) SEQUENCE DESCRIPTION: SEQ ID NO:22:

GCCGCTGCAC TGTGAAGCTC TC     22

( 2 ) INFORMATION FOR SEQ ID NO:23:

( i ) SEQUENCE CHARACTERISTICS:
        ( A ) LENGTH: 14 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:23:

CAGCAGGATA AGTA     14

( 2 ) INFORMATION FOR SEQ ID NO:24:

( i ) SEQUENCE CHARACTERISTICS:
        ( A ) LENGTH: 13 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:24:

GGTTACTGGA GAG    13

( 2 ) INFORMATION FOR SEQ ID NO:25:

( i ) SEQUENCE CHARACTERISTICS:
    ( A ) LENGTH: 15 bases
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:

(B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:25:

GTATCTGCAC AGAGG              15

(2) INFORMATION FOR SEQ ID NO:26:

(i) SEQUENCE CHARACTERISTICS:
            (A) LENGTH: 90 bases
            (B) TYPE: nucleic acid
            (C) STRANDEDNESS: single
            (D) TOPOLOGY: linear (ii) MOLECULE TYPE: other nucleic acid (iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION: /note= "DRB5*0101"

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:

(K) RELEVANT RESIDUES IN SEQ ID NO:

(xi) SEQUENCE DESCRIPTION: SEQ ID NO:26:

GGGGACACCC GACCACGTTT CTTGCAGCAG GATAAGTATG AGTGTCATTT  50

CTTCAACGGG ACGGAGCGGG TGCGGTTCCT GCACAGAGAC  90

(2) INFORMATION FOR SEQ ID NO:27:

(i) SEQUENCE CHARACTERISTICS:
        (A) LENGTH: 90 bases
        (B) TYPE: nucleic acid
        (C) STRANDEDNESS: single
        (D) TOPOLOGY: linear (ii) MOLECULE TYPE: other nucleic acid (iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION: /note= "DRB1*1201"

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:27:

GGGGACACCA GACCACGTTT CTTGGAGTAC TCTACGGGTG AGTGTTATTT  50

CTTCAATGGG ACGGAGCGGG TGCGGTTACT GGAGAGACAC  90

(2) INFORMATION FOR SEQ ID NO:28:

(i) SEQUENCE CHARACTERISTICS:
        (A) LENGTH: 90 bases
        (B) TYPE: nucleic acid
        (C) STRANDEDNESS: single
        (D) TOPOLOGY: linear (ii) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION: /note= "DRB1*0901"

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:28:

```
NNNNNNNNN  NNNNNNNNNN  NNNNNNNNNN  NNNNNNNNNN  NNNNNNNNNN    50

NTTCAACGGG  ACGGAGCGGG  TGCGGTATCT  GCACAGAGGC                90
```

( 2 ) INFORMATION FOR SEQ ID NO:29:

( i ) SEQUENCE CHARACTERISTICS:
        ( A ) LENGTH: 90 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION: /note= "DRB1*0101"

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:29:

```
GGGGACACCC GACCACGTTT CTTGTGGCAG CTTAAGTTTG AATGTCATTT    50
CTTCAATGGG ACGGAGCGGG TGCGGTTGCT GGAAAGATGC              90
```

MICROTITER WELL FOR DETECTING NUCLEIC ACID

This application is a continuation of now abandoned application Ser. No. 08/004,572, filed Jan. 14, 1993 abandoned, which is a continuation-in-part application of Ser. No. 07/722,673 filed Jun. 28, 1991 abandoned.

BACKGROUND OF THE INVENTION

1. Field of the Invention

The present invention relates to a microtiter well for detecting a nucleic acid in a biological sample. More particularly, this invention relates to a microtiter well which enables a target nucleic acid to be rapidly detected and the detection procedure to be automated.

2. Description of the Related Art

Hybridization processes for detecting a specific sequence of a nucleic acid include a solid-liquid hybridization process wherein nucleic acids adsorbed on a solid support are hybridized with nucleic acids contained in a solution; and a liquid-liquid hybridization process wherein target nucleic acids and nucleic acid probes contained in a solution are hybridized with each other (Anal. Biochem., 169, 1–25 (1988)). Up to now, these processes have been improved in various ways for the purpose of more easily, more rapidly and more sensitively detecting a target nucleic acid (Anal. Biochem., 169, 1–25 (1988)).

Among them, there is a proposal on a process wherein a microtiter well used in the field of immunoassay is utilized for automating the procedure of detecting a target nucleic acid (Japanese Patent Laid-Open Publication No. 219400/86). In this process, after double stranded DNA in a sample is converted to a single stranded form, the single stranded nucleic acids are immobilized through a nonspecific adsorption on a microtiter well under such a condition that complementary strands are present. Due to the inherent characteristic of DNA, some of the single stranded nucleic acids return to a double stranded form during the immobilization process and the subsequent hybridization process, so that in an actual hybridization the amount of the hybridizable DNA appears to be substantially smaller than that of immobilized DNA. Furthermore, in this process, the amount of DNA immobilized is relatively small. This renders the process unsatisfactory from the practical viewpoint.

Immobilization of polythymidylic acids on a microtiter well has been proposed as a capturing probe for sandwich hybridization process (Molecular and Cellular Probes, 3, 189–207 (1989)). This process is advantageous in that the amount of DNA immobilized is much larger than that in the case of a mixed base sequence of DNA by virtue of immobilization of a polymer of thymidylic acid having a higher reactivity than that of other nucleic acid bases in a photoreaction. The application of immobilized polythymidylic acids, however, is limited to a sandwich hybridization, so that the process suffers from the disadvantages of a complicated procedure and a lowered sensitivity inherent in the sandwich hybridization.

A nucleic acid amplification process called the PCR (Polymerase Chain Reaction) was developed in recent years. It is the epoch-making process which can amplify a minute amount of a certain gene by one hundred thousand times or more in a short time (U.S. Pat. No. 4,683,195). A proposal has been made on a process for detecting a mutation of human gene through the utilization of nucleic acids amplified by PCR (Proc. Natl. Acad. Sci., U.S.A., 86, 6230–6234 (1989)). The proposed process is called "reverse dot hybridization" and characterized by chemically synthesized oligonucleotides complementary to a base sequence to be detected and adding polythymidylic acid to the oligonucleotides by an enzymatic reaction to facilitate the immobilization of the oligonucleotide on a nylon membrane. This process has the advantage of the oligonucleotide being efficiently immobilized on a nylon membrane, but is disadvantageous in that the process in which use is made of a nylon membrane, as such, is unsuitable for automation of the detection procedure and the preparation of the immobilized probes are unsuitable for mass production.

Although the above processes have advantages in some results, they have respective drawbacks and no process capable of realizing a satisfactory simplicity, rapidity and high sensitivity has been developed in the art.

SUMMARY OF THE INVENTION

The present inventor has now found that a single stranded nucleic acid derived from a phage or a composite vector comprising a phage and a plasmid can be immobilized through a nonspecific adsorption in a microtiter well, and that the microtiter well in which the single stranded nucleic acids are immobilized can be used for detecting a target nucleic acid in a biological sample with a high sensitivity.

Accordingly, an object of the present invention is to provide a microtiter well capable of detecting a target nucleic acid in a biological simple, rapid and highly sensitive manner.

Another object of the present invention is to provide a microtiter well which enables a detection procedure to be automated.

According to a first aspect of the invention, there is provided a microtiter well for detecting the presence or absence of a target nucleic acid comprising a well in which a single stranded nucleic acid including a plurality of sequences specifically hybridizable with the target nucleic acid is immobilized, the single stranded nucleic acid being derived from a phage or a phage-plasmid.

The microtiter well according to the present invention enables a target nucleic acid to be specifically detected with a high sensitivity and high efficiency and further enables the detection procedure to be improved in simplicity and rapidity and to be automated.

BRIEF DESCRIPTION OF THE DRAWINGS

The aforesaid and other objects and features of the present invention will now become apparent from the following detailed description with reference to the accompanying drawings, in which:

FIG. 3 is a diagram showing nucleic acid sequences inserted into a vector for the preparation of an immobilized single stranded DNA in the detection of point mutation of β-thalassemia gene;

FIG. 5 is a graph showing the relationship between the number of oligonucleotide units of an immobilized probe and the sensitivity; and FIG. 6 is a diagram showing sequences of respective types of HLA-DB genes and a sequence of a probe used in Example 11.

DESCRIPTION OF THE PREFERRED EMBODIMENTS

Figure 1:
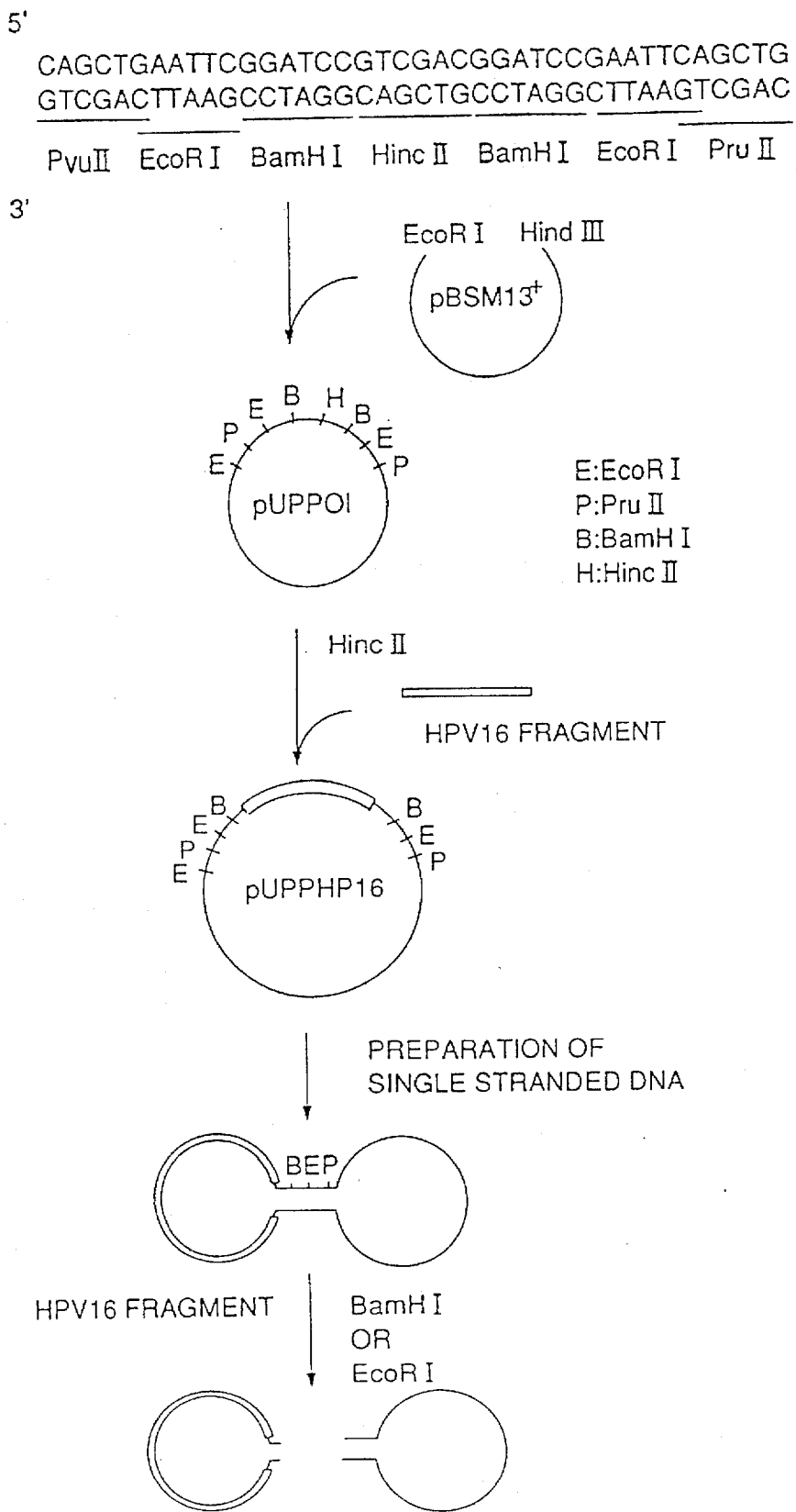
FIG. 1 is a diagram showing the construction of an improved vector for preparing a linear single stranded DNA and the preparation of the single stranded DNA.

The term "target nucleic acid to be detected" used herein is intended to mean a nucleic acid containing a specific base sequence to be detected and may be any of DNA and RNA. The nucleic acids to which the present invention is applicable can be prepared from every form of life including bacteria, viruses and higher plants and animals. The nucleic acids may be in a purified form or in an unpurified form.

In a nucleic acid detection process using a microtiter well of the present invention, not only a nucleic acid obtained from the above-described life but also a synthesized nucleic acid corresponding to a nucleic acid derived from the specimen or a synthesized nucleic acid complementary to the nucleic acid may be used as the target nucleic acid to be detected. Therefore, in the present invention, the "target nucleic acid" includes a nucleic acid in a biological sample to be detected, a synthesized nucleic acid corresponding to the nucleic acid in the biological sample and a synthesized nucleic acid complementary to the nucleic acid in the biological sample.

According to the present invention, single stranded nucleic acids specifically hybridizable with a target nucleic acid is immobilized on a microtiter well, preferably a polystyrene microtiter well. In the microtiter well, the immobilized single stranded nucleic acid are under such a condition that the strands complementary to the single stranded nucleic acids are absent.

In the present invention, a single stranded nucleic acid derived from a phage or a composite vector comprising a phage and a plasmid which contain a gene to be detected is used. Preferred examples of the phage and the composite vector include M13 phage, pUC118, pBSM13(±), pUCf1 (Methods in Enzymology, 153, 3–34, (1978)), pGEM-325 (±), pGEM-525(±), pGEM-725(±), pGEM-925(±), pGEM-1125(±), pGEM-1352(±), pGEMEX-1, pGEMEX-2, pSELECT-1 (available from PROMEGA), pT3/T7-3, pYEUra3 (available from CLONTECH), pKMN(±) (available from TOYOBO CO., LTD.), M13mp18/19, M13tu18/19, pUC118, pUC119, pTU118, pTU119, pTWU228, pTWU229 (available from TAKARA SHUZO CO., LTD.), pSL1180, pSL1190, pTZ18R, pTZ19R, pT7T3u18U, pT7T3u19U (available from PHARMACIA), pBluescript II SK(±), pBluescript II KS(±), pBc SK(±), pSc KS(±), pSluescript SK(±), pBluescript KS(±) and pBS (±) (available from STRATAGENE). Although the single stranded nucleic acid which is derived from the phage or the composite vector is immobilized in a circular form as it is, the single stranded nucleic acid can be digested to provide a linear form, preferably 1 k bs to 8 k bs fragment, and then immobilized.

According to another aspect of the present invention, the single stranded nucleic acid to be immobilized preferably contains a plurality of sequences hybridizable with a target nucleic acid. The presence of many sequences hybridizable with a target nucleic acid in a single stranded nucleic acid to be immobilized can shorten the time necessary for the hybridization, so that a gene can be rapidly detected.

The single stranded nucleic acid containing a plurality of sequences hybridizable with a target nucleic acid include can be prepared by introducing a plurality of sequences hybridizable with a target nucleic acid into the above-described phage DNA or a composite vector comprising a phage and a plasmid and producing a single stranded nucleic acid therefrom. In particular, it is preferred to use a single stranded nucleic acid prepared from a vector containing 5 to 200 copies of a sequence hybridizable with a target nucleic acid.

When a point mutation or the like in a nucleic acid sequence in a sample should be detected by hybridization, it is preferred that a sequence hybridizable with a target nucleic acid is relatively short.

The use of single stranded nucleic acids containing a plurality of sequences hybridizable with a target nucleic acid is advantageous in that the sequence hybridizable with the target nucleic acid can be immobilized in a relatively large amount.

It is known that an oligonucleotide immobilized on a solid support has a poor hybridization efficiency because the oligonucleotide immobilized on the solid support has a portion which participates in the immobilization on the support and cannot involve in hybridization. The hybridization efficiency of the immobilized oligonucleotides is, in general, lower than that attained in the solution. When use is made of single stranded nucleic acids prepared from the above-described vector containing a plural number of a unit sequence hybridizable with a target nucleic acid, a number of the unit sequences which do not involve in the immobilization on a solid support appear to be present. Thus, the lowering in the hybridization efficiency derived from the immobilization is advantageously small.

When labelling of a target nucleic acid is conducted by use of an elongation reaction or an amplification reaction and the labelled product to be detected, the single stranded nucleic acid to be immobilized is preferably less homologous to primers utilized for the elongation reaction or the amplification reaction. For example, in the PCR process, in many cases, the primer used in the gene amplification remains in the solution after the amplification reaction. In this case, it is necessary to select the sequence of the single stranded nucleic acid in such a manner that the primers do not hybridize with the single stranded nucleic acid. This is true of the other gene amplification methods.

It was surprising that the single stranded nucleic acids derived from the phages or the composite vectors comprising a phage and a plasmid which contain a gene to be detected can be directly immobilized on a microtiter well through a nonspecific absorption efficiently. In particular, the single stranded nucleic acids having 1 k bs to 8 k bs size can be directly immobilized on a microtiter well in a large amount. Thus, it is preferred to use the single stranded nucleic acids having 1 k bs to 8 k bs size. In addition, a microtiter well on which the single stranded nucleic acids having 1 k bs to 8 k bs size are immobilized ensures a detection of a target nucleic acid in a high sensitivity. The adsorption of the single stranded nucleic acid on the microtiter well can be preferably enhanced by irradiation of ultraviolet light or by adding $MgCl_2$ (Japanese Patent Laid-Open Publication No. 219400/1986).

In the nucleic acid detection process using a microtiter well according to the present invention, a target nucleic acid to be detected may be labelled. Examples of the labelling method include (1) a method wherein a label is directly introduced into a target nucleic acid, (2) a method wherein a nucleic acid corresponding to a target nucleic acid or a nucleic acid complementary to the target nucleic acid is synthesized with a labelled oligonucleotide primer and (3) a method wherein a nucleic acid corresponding to a target nucleic acid or a nucleic acid complementary to the target nucleic acid is synthesized with an oligonucleotide primer in the presence of a labelled nucleotide unit.

A method wherein a biotin derivative is introduced into a target nucleic acid by a photoreaction and a detection is conducted through an enzyme conjugated streptavidin (Nucleic Acids Res., 13, 745 (1985)); and a method wherein a target nucleic acid is sulfonated and detected through an enzyme conjugated anti-sulfon antibody (Proc. Natl. Acad. Sci., U.S.A., 81, 3466–3470 (1984)) are preferred as the above method (1) wherein a label is directly introduced into a target nucleic acid from the viewpoints of simplicity and rapidity of the procedure.

An amplification of a specific nucleic acid sequence (BIO/TECHNOLOGY, 8, 291 (1990)) may be utilized for the above methods (2) and (3). The methods have drawn attention particularly in respect of the amplification of a target nucleic acid and further are of a high value in relatively simple labelling of a synthesized nucleic acid corresponding to a target nucleic acid or a synthesized nucleic acid complementary to the target nucleic acid. For example, in the PCR process (Science, 230, 1350–1354 (1985)), a labelled elongation product or amplification product can be prepared with a labelled primer or labelled mononucleotides. In the amplification method wherein Qβ replicase is utilized (BIO/TECHNOLOGY, 6, 1197 (1988)), a labelled elongation product or amplification product can be prepared with similarly labelled mononucleotides. Also in the nucleic acid amplification method other than described above, an elongation product or an amplification product can be labelled with labelled mononucleotides or labelled oligonucleotides incorporated by an elongation reaction or an amplification reaction. The method (2) is preferred in the present invention.

The label used herein may be radioactive or non-radioactive as far as this substance can be detected after the hybridization procedure. A non-radioactive label is preferred from the viewpoint of handleability, storage stability and disposal and because it can exhibit most efficiently the effect of the present invention.

Examples of the non-radioactive label include haptens, such as biotin, 2,4-dinitrophenyl group and digoxigenin, fluorescent substances such as fluorescein, rhodamine, tetramethylrhodamine, sulfo rhodamine, 7-nitrobenz-2-oxa-1,3-diazole (NBD) and dansyl group or chemiluminescent substances such as acridine. An oligonucleotide can be labelled with the substance by any of known means (Japanese Patent Laid-Open Publications No. 204200/84 and Japanese Patent Nos. 1651975 and 1706289). When labelled nucleotides are used, the labelling can be conducted by known means (Proc. Natl. Acad. Sci., U.S.A., 80, 4045 (1983) and Japanese Patent Laid-Open Publication No. 152364/88). Alternatively, a commercially available product may be utilized.

The target nucleic acid labelled as described above is hybridized with the single stranded nucleic acid immobilized in a microtiter well.

The hybridization conditions may be properly selected and determined according to a combination of the target nucleic acid with the immobilized single stranded nucleic acid. For example, the hybridization can be basically conducted in the same manner as that wherein the conventional membranes may be used (B. D. Hames and S. J. Higgins, Nucleic Acid Hybridization, A Practical Approach, IRL Press (1985)).

The washing procedure after the hybridization reaction as well can be conducted in the same manner as that of the conventional process. Because of simplicity, it is preferred to conduct the washing procedure under such a condition that excess reagents etc. can be removed at room temperature.

In the detection of a point mutation, the washing conditions should be carefully determined. It is also useful to utilize such a condition wherein the stability of the duplex depends upon only the length of the complementary strand but does not upon the base composition of the complementary strand (Nucleic Acids Res., 16, 4637–4650 (1988)).

Simultaneously with or after the hybridization procedure described above, a target nucleic acid is detected through a label present in the target nucleic acid.

The detection procedure may be properly selected and determined according to the kind of the label present in the target nucleic acid.

When the label is directly detectable, that is, when the label is, for example, a radioisotope, a fluorescent substance or a dye, the detection procedure may be conducted in such a state that a labelled nucleic acid is bonded to a solid phase, or alternatively the detection procedure may be conducted by liberating the label into a solution in such a state that it is bonded to the nucleic acid or released from the nucleic acid and then conducting the detection according to the label. On the other hand, when the label is indirectly detectable, that is, when the label is a ligand capable of causing a specific binding reaction, such as biotin or hapten, the detection procedure can be conducted by a method commonly used in the detection of this type, that is, by use of an acceptor (for example, avidin or antibody) to which a label capable of directly generating a signal or an enzyme catalyzing a signal generating reaction has been bound. The acceptor may be previously added in the hybridization procedure. In this case, the binding process of the ligand to the acceptor can be conducted simultaneously with the hybridization step with the result that the whole process can be simplified.

It is advantageous that the microtiter wells according to the present invention enable a detection of a plural of biological samples simultaneously. It is also advantageous that the microtiter well according to the present invention enable the detection procedure to be automated.

EXAMPLES

The present invention will now be described in more detail by way of the following examples, though it is not limited to these examples only.

The procedure of the genetic engineering techniques in the following examples was conducted according to Molecular Cloning, the 2nd edition (T. Maniatis et al., Cold Spring Harbor Laboratory Press (1989)). Oligonucleotide was prepared by use of a model 381 A automatic synthesizer manufactured by Applied Biosystems, Inc. and subjected to deprotection reaction and purification before use by the conventional procedure (Oligonucleotide Synthesis, IRL Press (1984)). The biotin-labelted oligonucleotide was prepared by adding Aminolink II (trademark) (manufactured by Applied Biosystems, Inc.) to oligonucleotide in the final stage of the synthesis of the oligonucleotide to introduce an amino group into the oligonucleotide, and reacting the oligonucleotide with biotin succinimide ester according to the method described in U.S. Patent No. 4,849,336.

Example 1

Preparation of single stranded DNA for immobilization

A linear single stranded DNA was prepared by a modified method of Messing et al. (Methods in Enzymology, 101, Part C, 20 (1983)). A chemically synthesized DNA fragment shown in FIG. 1 (SEQ ID NO. 1) was inserted into between EcoRI and Hind III sites of plasmid pBSM13+ (manufactured by Stratagene Cloning Systems, Inc.) to prepare plasmid pUPPO1. Then, a 1.8 kb fragment containing genes E6 and E7 of human papilloma virus 16 was inserted into a Hinc II site of this plasmid to prepare plasmid pUPPHP16. *E. coli* NM522 was transformed with the plasmid, and a single stranded DNA was prepared by the conventional procedure with helper phage M13K07 (Methods in Enzymology, 153, 3–34 (1987)).

The single stranded DNA was cleaved by restriction enzyme EcoRI or BamHI for linearization.

Example 2

Immobilization of single stranded DNA in microtiter well

The single stranded DNA prepared in Example 1 was dissolved in a solution of 10 mM Tris.HCl, pH 7.6, and 1 mM EDTA to a concentration of 100 ng/µl and then mixed with a four-fold volume of $H_2O$ and a five-fold volume of an immobilization buffer (1.5M NaCl, 0.3 M Tris.HCl, pH 8.0, 0.3M $MgCl_2$). The mixture was added to microtiter wells (Dynatech, Immulon 2, removawell strips, No. 011-010-6302) in an amount of 100 µl per well. The wells were covered and allowed to stand at 37° C. for 16 hr. Then, the liquid was removed, and the wells were air-dried at 37° C. for 30 min and subjected to light irradiation of 500,000 µJ through the use of Stratalinker (trademark) 2400 (manufactured by Stratagene Cloning Systems, Inc.). After the irradiation, the wells were washed three times with a washing buffer (1M NaCl, 2 mM $MgCl_2$, 0.1M Tris.HCl, pH 9.3, 0.1% Tween 20:200 µl). The wells were then sealed in a polyvinyl chloride bag and stored at 4° C.

Example 3

Hybridization in microtiter well and detection

A hybridization solution (5×SSC, 5×Denhardt's solution, 0.2% SDS, 200 µg/ml, salmon sperm DNA: 100 µl/well) was added to the microtiter wells in which the single stranded DNA containing a human papilloma virus 16 gene prepared in Example 2 had been immobilized, and further a dilution of biotin-labelled oligonucleotides (Bio-ATTGTAATGGGCTCTGTCCG, 20 ng/well (SEQ ID NO. 2) which are complementary to part of the human papilloma virus 16 gene was added thereto. The mixture was maintained at 55° C. for 30 min. The hybridization solution was removed, and the wells were washed three times with 2×SSC (200 µl/well). A streptavidin-alkaline phosphatase solution (prepared by subjecting a solution of streptavidin-alkaline phosphatase (Bethesda Research Laboratories, Inc.) to 1,000-fold dilution with 0.1M Tris.HCl, pH 7.5, 0.3M NaCl, 2 mM $MgCl_2$, 0.05% (v/v) Triton X-100) was added thereto (100 µl/well), and the wells were shaken at 23° C. for 10 min. The reaction mixture was removed from the wells, and the wells were washed three times with a washing solution (0.1M Tris.HCl, pH 7.5, 0.3M NaCl, 2 mM $MgCl_2$, 0.05% (v/v) Triton X-100: 200 µl/well). After the washing, a p-nitrophenyl phosphate solution (1M diethanolamine, pH 9.8, 0.5 mM $MgCl_2$: 4 mg/ml: 100 µl/well) was added to the wells and a reaction was allowed to proceed at 23° C. for one hr. Absorbance was then measured at 405 nm. The results are given in Table 1.

TABLE 1

| Well No. | Absorbance (at 405 nm) |
|---|---|
| 1 | 1.34 |
| 2 | 0.13 |
| 3 | 0.13 |

Well No. 1: the well in which the single stranded nucleic acid containing a human papilloma virus sequence was immobilized.
Well No. 2: the well in which the single stranded nucleic acid unrelated to a human papilloma virus sequence was immobilized.
Well No. 3: the well in which no DNA was immobilized.

In the table, the absorbance were corrected by subtracting the background at 405 nm.

Example 4

Effect of UV irradiation on immobilization of DNA in microtiter well

The plasmid DNA (pUPPHP16) and the single stranded DNA prepared therefrom prepared in Example 1 were linearized by cleaving with EcoRi and then immobilized in microtiter wells in the same manner as that of Example 2. In this case, when the double stranded DNA, i.e., pUPPHP16, was immobilized, heat denaturation was conducted before the double stranded DNA was mixed with the immobilization buffer. Then, two types of microtiter wells were prepared. Specifically, in one, UV irradiation was conducted in the same manner as that of Example 2, and in the other, no UV irradiation was conducted. The hybridization capability of the wells thus prepared was examined with the oligonucleotides, Bio-ATTGTAATGGGCTCTGTCCG (SEQ ID NO. 2), in the same manner as that of Example 3. The results are given in Table 2.

TABLE 2

| Well No. | Absorbance (at 405 nm) |
|---|---|
| 1 | 1.58 |
| 2 | 0.58 |
| 3 | 0.51 |
| 4 | 0.48 |

Well No. 1: the well in which the single stranded DNA was immobilized with UV irradiation.
Well No. 2: the well in which the single stranded DNA was immobilized without UV irradiation.
Well No. 3: the well in which the double stranded DNA was immobilized with UV irradiation.
Well No. 4: the well in which the double stranded DNA was immobilized without UV irradiation.

In the table, the absorbance were corrected by subtracting the background at 405 nm.

Example 5

Comparison of hybridization capability after immobilization in microtiter well of single stranded DNA with that of double stranded DNA The hybridization capability after immobilization in a microtiter well of a single stranded DNA was compared with that of a denatured double stranded DNA. The single stranded DNA and the double stranded DNA were prepared in substantially the same manner as that of Example 4, but the single stranded DNA were immobilized in a cyclic form.

Figure 2:
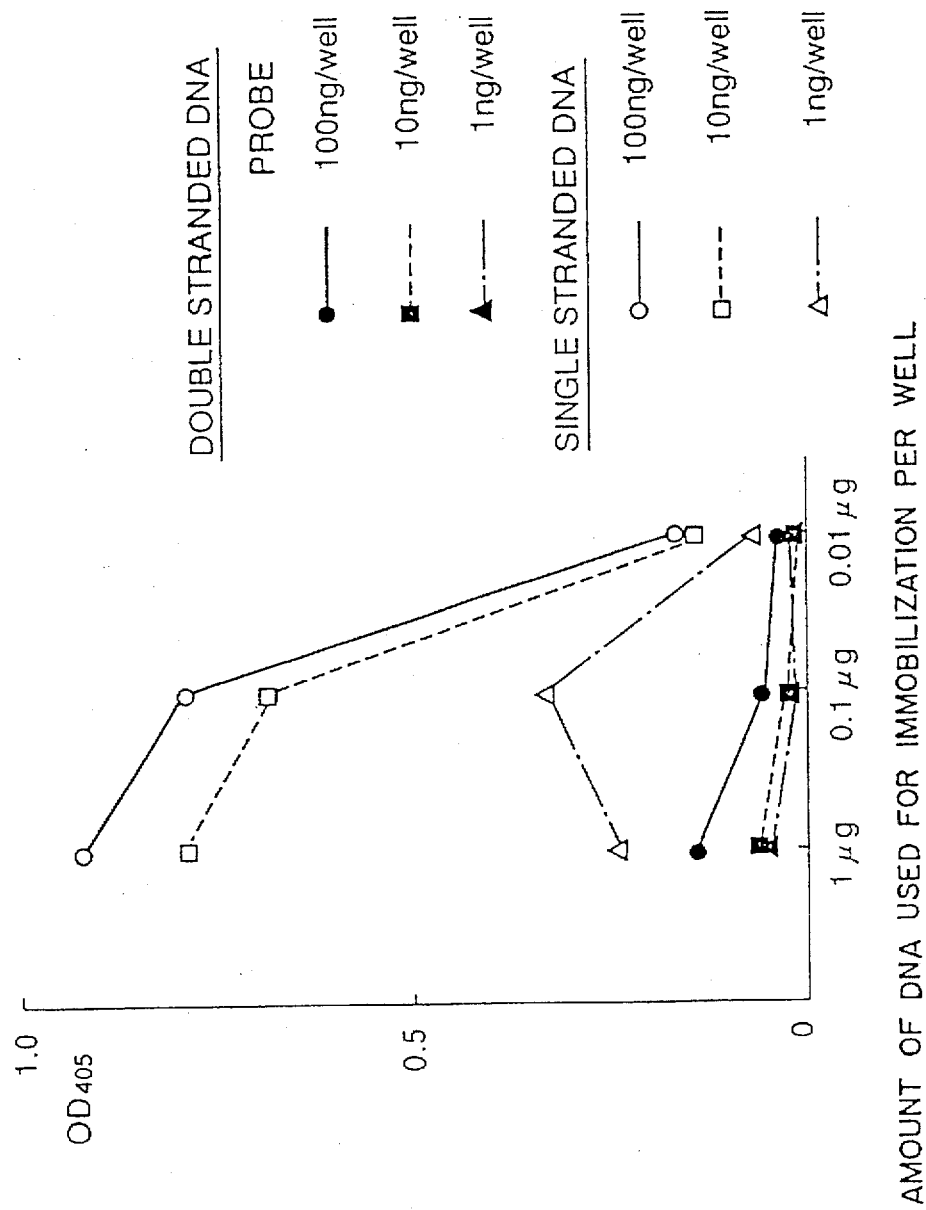
FIG. 2 is a graph showing the results of a comparison of the hybridization efficiency on a single stranded DNA immobilized on a microtiter well with that on a double stranded DNA immobilized on a microtiter well.

The DNA solution was added in an amount of 1 µg, 100 ng and 10 ng each per well for the immobilization in the same manner as that of Example 2. The hybridization capability of each well was examined by use of Bio-ATTGTAATGGGCTCTGTCCG (SEQ ID NO. 2) as a probe in the same manner as that of Example 3. The results were as shown in FIG. 2 (the absorbance at 405 nm were measured by a microplate reader).

Example 6
Labelling by gene amplification and detecting amplification product and point mutation An oligonucleotide corresponding to codons 2 through 11 of a human β-globin was chemically synthesized and inserted into a HincII site of plasmid pUCf1 (see FIG. 3). The procedure was conducted for both a normal gene (βA) (SEQ ID NO. 3) and a point mutated gene (βS) (SEQ ID NO. 4) causative of β-thalassemia. Among the resultant clones, a clone capable of providing a sense single stranded DNA was selected, and the single stranded DNA was prepared therefrom. The single stranded DNA thus were immobilized in a cyclic form in microtiter wells according to the procedure described in Example 2.

Then, a gene amplification was conducted. The reaction was conducted through the use of GeneAmp (trademark) manufactured by Cetus Corporation according to the protocol by the manufacturer. 5' ACACAACTGTGTGTTCAC-TAGC (SEQ ID NO. 5) and biotinylated Bio-CAACTTCATCCACGTTCACC (SEQ ID NO. 6) were used as the primer, and 4.4 kb DNA fragments prepared from the plasmid DNA (pBR322-HβPst) by the digestion of Pst I (DNA, 3, 7-15 (1984)) was used as the template.

After the gene amplification, an aliquot of the reaction mixture was heat-denatured and subjected to hybridization and subsequent detection in the same manner as that of Example 3. The results are given in Table 3 (the absorbance at 405 nm were measured by a microplate reader).

TABLE 3

| Well No. | Absorbance (at 405 nm) |
| --- | --- |
| 1 | 0.432 |
| 2 | 0.288 |
| 3 | 0.037 | well No. 1: the well in which the single stranded DNA containing A-gene was immobilized.
well No. 2: the well in which the single stranded DNA containing S-gene was immobilized.
well No. 3: the well in which the single stranded DNA unrelated to -globin gene was immobilized.

In the table, the absorbance were corrected by subtracting the background at 405 nm.

Figure 4:
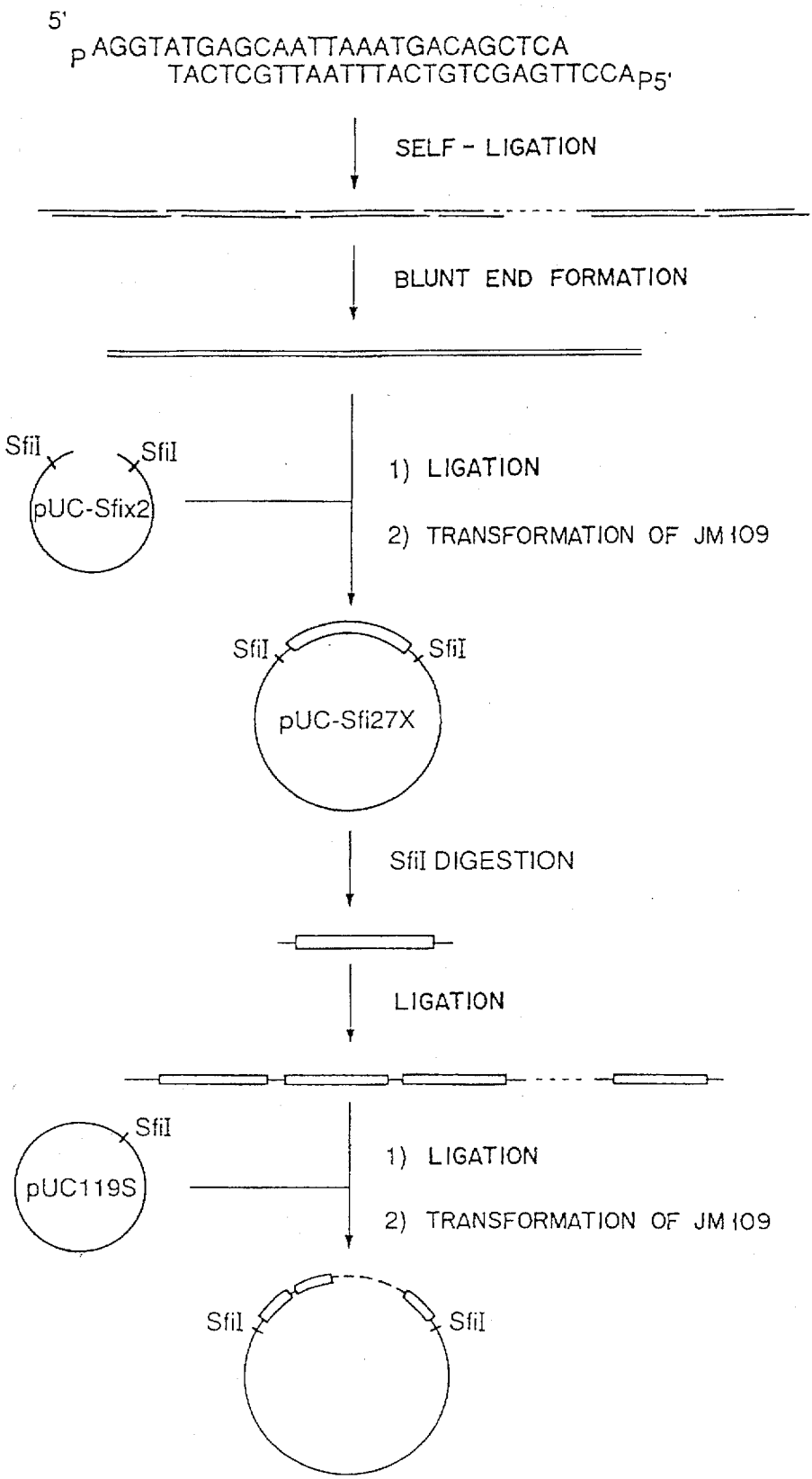
FIG. 4 is a diagram showing the preparation of a plasmid vector containing repetition of a oligonucleotide unit complementary to a human papilloma virus 16 gene.

Example 7
Preparation of single stranded DNA containing repetition of unit sequence A part of E7 gene of human papilloma virus 16 was chemically synthesized, and single stranded DNA containing repetition of a sequence of the synthesized oligonucleotides (the unit sequence) was prepared therefrom according to the method shown in FIG. 4 (SEQ ID NO. 7).

Briefly, two kinds of oligonucleotides shown in FIG. 4 were chemically synthesized, and the 5' terminal thereof was phosphorylated with polynucleotide kinase and ATP. Then, the two kinds of oligonucleotides were mixed with each other to form a double strand. The fragments of the double strand were linked to each other with T4 DNA ligase. After the ligation, blunt ends were formed by use of the Klenow fragment of E. coli DNA polymerase and four kinds of deoxynucleoside triphosphates. The resultant reaction product was electrophoresed on 6% polyacrylamide gel, and a portion corresponding to 270 bp was cut out to recover DNA.

Then, plasmid pUC-Sfix2 (Japanese Patent Laid-Open Publication No. 190194/90) was cleaved by BamHI, and the terminal 5' phosphate was removed with alkaline phosphatase. This product was ligated with T4 DNA ligase to the DNA recovered from the polyacrylamide gel. E. coli JM109 was transformed with the ligated product. An stable clone was selected with ampicillin marker. The plasmid pUC-Sfi27x thus obtained was cleaved by SfiI, and a portion containing repetition of the unit sequence was purified and recovered by electrophoresis. This fragment was self-ligated with T4 DNA ligase and inserted into the SfiI site of plasmid pUC119S (prepared by inserting SfiI linker (manufactured by Boehringer Mannheim; #909785) into the BamHi site of pUC119). Clones are different from each other in the number of the unit sequence depending upon the degree of self-ligation. In the present experiment, clones wherein the numbers of the unit sequence is 9, 14, 64 and 165 were obtained.

Example 8
Effect of probe into which oligonucleotide has been repeatedly inserted Single stranded DNAs were prepared respectively from the clone prepared in Example 7 and a separately prepared clone having one unit sequence in the same manner as that of Example 1 and immobilized in a microtiter well in the same manner as that of Example 2.

Then, the following gene amplification was conducted by using the following two biotin-labelled primers:

Bio-GCAACCAGAGACAACTGATC (SEQ ID NO. 8)

Bio-ATTGTAATGGGCTCTGTCCG (SEQ ID NO. 2)

and a plasmid containing a E7 gene of papilloma virus 16 (HPV16) as a template.

GeneAmp (trademark) manufactured by Cetus Corporation were added to 10 ng of plasmid pUPPHP16 (see Example 1) and 100 ng of each primer according to the protocol by the manufacturer, and the total volume of the reaction solution was adjusted to 100 μl with water. The reaction solution was heated at 95° C. for 5 min in a thermal cycler manufactured by Perkin-Elmer Cetus Instruments, Inc. to denature DNA, and 2.5 units of AmpliTaq (trademark) was added thereto. The cycle of heating at 72° C. for 60 sec, at 94° C. for 30 sec and at 50° C. for 30 sec was repeated 30 times.

The reaction mixture was diluted with water and 5 μl of the diluent was heat-denatured and hybridized with a previously prepared microtiter wells on which the single stranded DNA containing a E7 gene sequences has been immobilized under the same condition as that described in Example 3, and the absorbance was measured.

The results are shown in FIG. 5. As is apparent from the drawing, when the number of the unit sequence was 64 or 165, the sensitivity was about 20 times that in the case where the number of the unit sequence was one.

Example 9
Detection of human papilloma virus 16 gene in rapid and simple manner In order to simplify the hybridization process of the present invention further, studies were conducted on the composition of the hybridization solution, hybridization temperature and color development time. According to results of the studies, the detection of a human papilloma virus 16 gene was conducted under the following simplified conditions.

10 ng of DNA extracted from Caski cells as a positive sample and 10 ng of DNA extracted from human peripheral blood as a negative sample were each used as a template, and gene amplification was conducted by the PCR process in the same manner as that of Example 8. The resultant reaction mixtures were added to wells prepared in Example 8. In one well single stranded DNA wherein the number of repetitions of the unit sequence was one had been immobilized, and in the other well, single stranded DNA wherein the number of repetitions of the unit sequence was 64 had been immobilized. Hybridization was conducted in 100 μl of a hybridization solution (5×SSC, 0.2% SDS) with 5 μl of the above-described PCR mixture at 37° C. for 30 min. After the hybridization solution was removed from the wells, the wells were washed three times with 200 μl of a washing solution (2×SSC).

A streptavidin-alkaline phosphatase solution (prepared by subjecting a solution of streptavidin-alkaline phosphatase (manufactured by Bethesda Research Laboratories, Inc.) to 1,000-fold dilution with 0.1M Tris.HCl, pH 7.5, 0.3M NaCl, 2 mM MgCl$_2$, 0.05% (v/v) Triton X-100) was added thereto 100 μl/well, and the wells were gently shaken at 23° C. for 10 min. After the solution was removed from the wells, the wells were washed three times with a washing solution (0.1M Tris.HCl, pH 7.5, 0.3M NaCl, 2 mM MgCl$_2$, 0.05% (v/v) Triton X-100: 200 μl/well). After the washing, 100 μl of p-nitrophenyl phosphate solution (1M diethanolamine, pH 9.8, 0.5 mM MgCl$_2$: 4 mg/ml) was added to the wells and an enzymatic reaction was allowed to proceed at 23° C. for 20 min. The absorbance was then measured at 405 nm. The results are given in Table 4. As is apparent from Table 4, even when the procedure was simplified, the positive sample could be significantly distinguished from the negative sample in the case of single stranded DNA wherein the number of the unit sequence was 64.

TABLE 4

| Well No. | Absorbance (at 405 nm) | |
| --- | --- | --- |
| | Positive sample (from Caski cell) | Negative sample (from normal human) |
| 1 | 0.04 | 0.00 |
| 2 | 0.73 | 0.02 |

Well No. 1: the well in which the single stranded DNA containing one unit sequence was immobilized.
Well No. 2: the well in which the single stranded DNA containing 64 repeats of the unit sequence was immobilized.

In the table, the absorbance were corrected by subtracting the background at 405 nm.

Example 10
Detection of mutation of HLA-DRB gene

Unit sequences as shown in Table 5, i.e., probes 1 to 12, were repeatedly ligated in the same manner as that of Example 7 and immobilized in microtiter wells, respectively. The probes are completely matched to a gene sequence of genotypes as shown in Table 5. The unit sequences in the single stranded nucleic acids are repeated sixty times.

TABLE 5

| Probe | Sequence | Genotype | SEQ ID NO. |
| --- | --- | --- | --- |
| 1 | CGG TTG CTG GAA AGA TGC | DR1 | 9 |
| 2 | CAG CAG GAT AAG TAT GAG | DR2 | 10 |
| 3 | GGC CGG GTG GAC AAC TAC | DR3 | 11 |
| 4 | TTG GAG CAG GTT AAA CAT | DR4 | 12 |
| 5 | T GAT GAG GAG TAC TGG AA | DR5(W11) | 13 |
| 6 | GG TTA CTG GAG AGA CAC T | DR5(W12) | 14 |
| 7 | TTC TTG GAG TAC TCT ACG | DR3,DR5,DR6,DR8 | 15 |
| 8 | TGG CAG GGT AAG TAT AAG | DR7 | 16 |
| 9 | A GAC AGG CGG GCC CTG GT | DR8 | 17 |
| 10 | G TAT CTG CAC AGA GGC AT | DR9 | 18 |
| 11 | TTG AAG CAG GAT AAG TTT | DR10 | 19 |
| 12 | TGC AGA CAC AAC TAC GGG | nonspecific (all genotypes) | 20 |

A gene amplification of HLA-DRB gene was conducted in the same manner as that of Example 8 by use of 1 μg of DNA extracted from human peripheral blood as a template and biotin-labelled primers as follows:

GLPDRB1 Bio-TTCTTCAATGGGACGGAGCG (SEQ ID NO. 21)

GAMPDRB1 Bio-GCCGCTGCACTGTGAAGCTCTC (SEQ ID NO. 22)

(GLPDRB1 is corresponding to amino acids 17 through 23 of HLA-DRB and GAMPDRB1 is corresponding to amino acids 87 to 94 of HLA-DRB, J. Exp. Med., 169, 2263–2267, 1989)

The gene amplification reaction cycle of heating at 94° C. for 30 sec, at 50° C. for 30 sec and at 72° C. for 60 sec was repeated 30 times. 5 μl of the reaction mixture was added to the microtiter wells on which probes 1 to 12 had been immobilized, and the hybridization was conducted at 60° C. for one hr and the enzymatic reaction was conducted at 23° C. for one hr. Other detailed procedure was as same as that of Example 3.

Absorbance measured at 405 nm are given in Table 6. According to the results, genotypes of the samples are determined as given in the table.

TABLE 6

| Sample | 1 | 2 | 3 | 4 | 5 | 6 | 7 | 8 | 9 | 10 | 11 | 12 | Genotypes |
| --- | --- | --- | --- | --- | --- | --- | --- | --- | --- | --- | --- | --- | --- |
| a | 1.69 | 1.03 | 0.12 | 0.16 | 0.12 | 0.15 | 0.13 | 0.18 | 0.19 | >2 | 0.08 | >2 | DR1 DR9 |
| b | 0.06 | >2 | 0.11 | 0.19 | 0.11 | 0.17 | 1.81 | 0.16 | 0.95 | 0.99 | 0.09 | >2 | DR2 DR8 |
| c | 0.06 | 0.23 | 1.51 | >2 | 0.08 | 0.50 | >2 | 0.12 | 0.16 | 0.09 | 0.06 | >2 | DR3 DR4 |
| d | 0.12 | 0.18 | 0.12 | 0.17 | 1.83 | 0.65 | >2 | 0.20 | 1.15 | 0.11 | 0.09 | >2 | DR5(W11) DR8 |
| e | 0.07 | 0.17 | 0.14 | 0.13 | 0.09 | >2 | >2 | 0.16 | >2 | 0.11 | 0.07 | >2 | DR5(W12) DR8 |
| f | 0.09 | 0.29 | 0.09 | 0.18 | 0.11 | 0.58 | >2 | >2 | 0.23 | 0.11 | 0.06 | >2 | DR6 DR7 |
| g | 0.28 | 0.27 | 0.08 | 0.19 | 0.10 | 0.15 | >2 | 0.20 | >2 | 0.11 | >2 | >2 | DR8 DR10 |

Example 11

Detection of mutation of HLA-DRB gene

Short Oligonucleotides, i.e., Probes A (SEQ ID NO. 23), B (SEQ ID NO. 24) and C (SEQ ID NO. 25) shown in FIG. 6, are immobilized in microtiter wells in the same manner as that of Example 2. Long Oligonucleotides, i.e., single stranded nucleic acids containing probes A, B and C sequence repeated 60 times, were prepared and then immobilized in microtiter wells, respectively, in the same manner as that of Example 7. Probes A, B and C are completely matched to gene sequences of genotypes DRB5*0101(SEQ ID NO. 26), DRB1*1201 (SEQ ID NO. 27) and DRB1*0901 (SEQ ID NO.28), respectively.

A gene amplification of HLA-DRB gene was conducted in the same manner as that of Example 10 to prepare Sample 1, 2 and 3. The hybridization procedure was conducted in the same manner as that of Example 3. Absorbance measured at 405 nm are given in Table 6. Although the short oligonucleotides have nonspecificity to the samples, each of the long oligonucleotides has a definite specificity to the samples. According the absorbance obtained with the long oligonucleotides, genotypes of the samples are determined as given in the table.

TABLE 7

| | Absorbance (at 405 nm) | | | | | | |
|---|---|---|---|---|---|---|---|
| | Short Oligonucleotides | | | Long Oligonucleotides | | | |
| Sample | Probe A | Probe B | Probe C | Probe A | Probe B | Probe C | Genotype |
| 1 | 0.193 | 0.139 | 0.180 | 2.520 | 0.216 | 0.238 | DRB5*0101 |
| 2 | 0.112 | 0.104 | 0.268 | 0.859 | 0.176 | 1.998 | DRB1*1201 |
| 3 | 0.212 | 0.204 | 0.160 | 0.311 | 1.695 | 0.249 | DRB1*0901 |

The results demonstrate that the long oligonucieotides on the microtiter wells has an advantage of typing the HLA-DRB gene compared with the short oligonucleotides.

What is claimed is:

1. A process for immobilizing an HLA-DRB oligonucleotide sequence in a microtiter well, comprising the steps of:

preparing a base sequence in which HLA-DRB oligonucleotide sequences specifically hybridizable with a target nucleic acid are repeated in tandem 5 to 200 times, inserting the base sequence into a vector which is capable of producing a single stranded nucleic acid to prepare a recombinant vector, transforming a microorganism with the recombinant vector, and culturing the microorganism to amplify the number of the base sequence, isolating the amplified base sequence in which the HLA-DRB oligonucleotide sequences specifically hybridizable with the target nucleic acid are repeated in tandem 5 to 200 times, and immobilizing the amplified base sequence in the microtiter well by irradiating the microtiter well in the presence of the amplified base sequence with ultraviolet light.

2. The process according to claim 1, wherein the vector is a phage or a phage-plasmid.

3. A microtiter well which is produced by the process of claim 1.

4. A microtiter well which is produced by the process of claim 2.

* * * * *